United States Patent [19]

Fry et al.

[11] Patent Number: 5,237,870
[45] Date of Patent: Aug. 24, 1993

[54] STRESS WAVE METHOD AND APPARATUS FOR ESTIMATING THE STRUCTURAL QUALITY OF FINGER JOINTS

[75] Inventors: Ray L. Fry, Colfax, Wash.; Friend K. Bechtel, Moscow, Id.; James D. Logan, Pullman, Wash.

[73] Assignee: Metriguard Inc., Pullman, Wash.

[21] Appl. No.: 764,500

[22] Filed: Sep. 20, 1991

[51] Int. Cl.$^5$ ............................................. G01N 29/04
[52] U.S. Cl. ...................................... 73/588; 73/598; 73/600; 73/618
[58] Field of Search ................. 73/588, 597, 598, 599, 73/600, 618, 827, 847, 849, 852; 209/518

[56] References Cited

U.S. PATENT DOCUMENTS

| | | | |
|---|---|---|---|
| 3,384,767 | 5/1968 | Arnold et al. | 73/600 |
| 3,423,991 | 1/1969 | Collins | 73/600 |
| 3,664,180 | 5/1972 | McDonald et al. | 73/598 |
| 4,201,093 | 5/1980 | Logan | 73/618 |
| 4,750,368 | 6/1988 | Shearer et al. | 73/618 |
| 4,838,085 | 6/1989 | Pellerin et al. | 73/597 |
| 4,856,334 | 8/1989 | Shearer et al. | 73/618 |

OTHER PUBLICATIONS

J. Krautkramer et al., *Ultrasonic Testing of Materials* (Springer-Verlag, New York, 1983), pp. 563-565.

Metriguard Inc. brochure, "Model 2600 Veneer Tester".

Metriguard Inc. brochure, "Model 239A Stress Wave Timer".

Faoro, Oscar, "Proof Loading to Establish the Structural Integrity of Finger Joints".

Eby, Robert E., "Proofloading of Finger-Joints for Glulam Timber", *Forest Products Journal*, Jan. 1981, pp. 37-41.

Logan, James D., "Proof Load Testing Finger End-Joined Lumber Tension or Bending?".

Bechtel, Friend K., "Proof Test Load Valve Determination for Maximum Economic Return", *Forest Products Journal*, Oct. 1983, pp. 30-38.

Pellerin, R. F., & Morschauser, "Nondestructive Testing of Particleboard", presented at 7th Washington State University Symposium on Particleboard, Mar. 1973.

*Primary Examiner*—John E. Chapman

[57] ABSTRACT

Method and apparatus are described for using stress wave measurements in the estimation of quality of finger joints in wood and quality of lumber, where quality is typically defined as strength. Application and measurement of stress waves in the transverse direction of the material allows localized measurements to be made, and features developed from this information are used in the quality estimation. A feature is a quantifiable characteristic developed from stress wave signals which can be used either by itself or in combination with other features to estimate quality. Examples of features include the propagation velocity of a stress wave, the attenuation of a stress wave, the difference in stress wave propagation times measured at different locations along the lumber, and the effects on amplitude and phase of frequency components of a stress wave. Treating features together as a feature vector and as input to an estimator function, estimated quality can be evaluated. The ability of the method and apparatus can be improved in some cases by performing the stress wave measurements in the presence of externally applied bending, tensile or torsional stress.

28 Claims, 11 Drawing Sheets

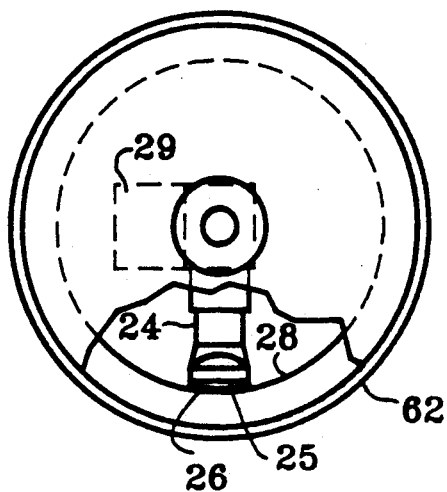
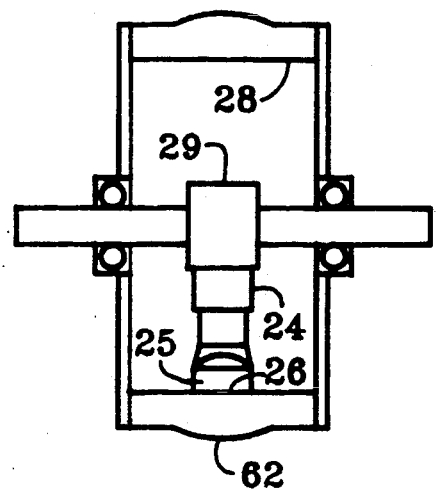
FIG 3  FIG 4
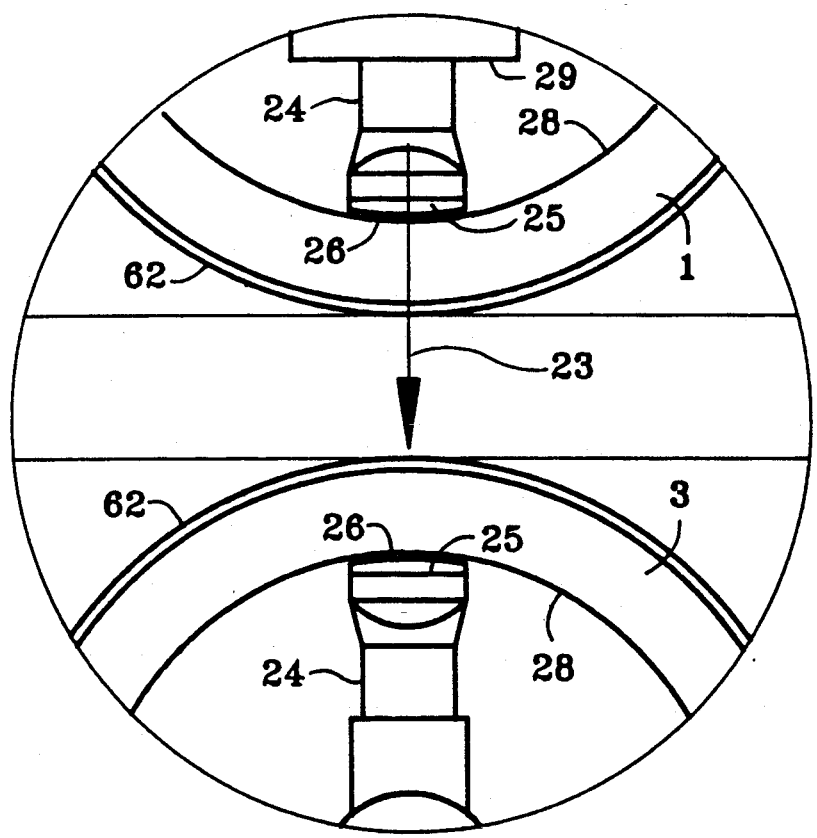
FIG 5

STRESS WAVE METHOD AND APPARATUS FOR ESTIMATING THE STRUCTURAL QUALITY OF FINGER JOINTS

TECHNICAL FIELD

The invention pertains to method and apparatus for measuring properties of stress waves in wood finger joints and the estimation of finger joint quality.

BACKGROUND OF THE INVENTION

Finger-joining short pieces of lumber together at their ends to make longer pieces of lumber is becoming ever more important as attempts are made to more efficiently use the lumber resource. In finger joining, matching interleaving fingers are cut into the ends of the members to be joined, adhesive is applied to the surfaces of the fingers, the parts are joined and longitudinal compressive force is applied while the adhesive cures. In some cases, short sections of lumber are left over as a by-product of production trimming operations. In other cases, the "shorts" result from cutting out naturally occurring defects. In still other cases longer lumber than the standard lengths available from normal sawmill operations is desired. In any event the economic value of short pieces is low, even if the inherent wood quality is high. Finger-joining the shorts into longer pieces is one method for increasing their value. In some applications, such as for studs in walls, finger-joined lumber may actually be more valuable than the competing one-piece studs they replace because the finger-joined product is generally straighter.

While the application of finger-joined lumber in studs is an important one, finger-joined lumber is also being used in more structurally demanding applications such as in trusses where large tensile or bending loads may be applied. By cutting out strength reducing characteristics such as knots and finger-joining the remaining short pieces, long pieces can be obtained without the strength reducing characteristics. But, this requires that the finger joints themselves be structurally sound. In these applications, finger-joined lumber must have sufficient quality to withstand design loads plus some margin of safety. As a result, interest has developed concerning methods of testing the finger joints. Finger joints can also be used to join other wood products including laminated veneer lumber and panel products as well as lumber.

In this disclosure, the term wood refers to any product made from wood fiber which includes wood timbers of all sizes, reconstituted wood products such as laminated veneer lumber and panel products. Finger joint quality refers generally to the structural quality of the finger joint. Usually, this will mean bending or tensile strength, but it could refer to any of the other structural properties such as compression strength, shear strength or bending modulus of elasticity.

Off-line tests of finger joint quality can be done on a sampling basis. The reasoning is that poor finger joints result from something going wrong in the process. Consistent process problems usually will be detected by testing production samples. Off-line tests may consist of applying increasing tensile loads to the wood through the finger joint, measuring the ultimate tensile load at failure and inspection of failed areas in the finger joint. Alternatively a fixed proof load equal to some factor above the design load can be applied to the wood and through statistical means, the number of failures can be used to define finger joint quality. However, any off-line quality control testing of finger joints which does not test all of production leaves some risk of missing significant problems in the joints. Production-line testing of every joint is a better approach.

Production-line proof load tests are possible wherein either bending or tensile stresses are applied. Both types of equipment have been proposed for use and have been put to work in the production-line (Faoro, Oscar, 1985. Proof Loading to Establish the Integrity of Structural Finger Joints. Fifth Nondestructive Testing of Wood Symposium. Pullman, Washington. and Eby, R. E., 1981. Proofloading of Finger-joints for Glulam Timber. Forest Prod. J. 31(1):37–41.), although technical arguments have been made in favor of tensile proof load testing (Logan, James D., 1982. Proof Load Testing Finger End-Joined Lumber Tension or Bending?. Metriguard Inc. Pullman, Washington.). Production-line proof load testing in either bending or tensile modes requires considerable space and leads to other problems as well. Among them are the handling of broken wood product as a result of applying the proof load and the continuity of production when a failure occurs. Perhaps the most severe problem, particularly in the case of bending proof testing, is the risk of overstressing the finger joint because of incomplete adhesive cure at the point in the production-line where testing is most convenient and hence most often performed.

The present invention avoids the problem of overstressing the finger joints by nondestructively passing stress waves in a transverse direction through the finger joints and processing the resulting signals to give a measure of finger joint quality. Further, the apparatus can be implemented more efficiently and conveniently in much less space in the production line than can proof testing equipment. This nondestructive method will not eliminate the need for tension proof testing in those cases where stress testing of every piece is necessary; rather it gives a predictive measure of finger joint quality. In many cases that will be a sufficient indication of finger joint quality. In other cases the prediction can be used to adjust the amount of tensile proof load applied and hence determine the final grade of the product, assuming it survives the proof load. The economics of the process of predicting strength from a correlated variable and adjusting the proof load to fit has been studied (Bechtel, F. K. 1983. Proof Test Load Value Determination for Maximum Economic Return. Forest Prod. J. 33(10):30–38.).

Testing of wood and other materials by measuring stress wave propagation time (or velocity) by either acoustic or ultrasonic means has long been used. Commercial examples include the Metriguard Model 239A Stress Wave Timer and the Metriguard Model 2600 Ultrasonic Veneer Grader, U.S. (Logan, James D., U.S. Pat. No. 4,201,093). Other things being equal, stress waves pass through structurally higher quality materials faster than they do through poorer quality materials. This is the basis of the Model 2600 Veneer Grader which grades according to the propagation time of an ultrasonic stress wave from one end of a veneer sheet to the other. Recently, in an attempt to nondestructively quantify the quality of finger joints, the present invention was conceived. The invention involves passing stress waves transversely through the finger joints with a modified version of the Model 2600 Veneer Grader transducer wheels. These wheels had previously been modified to focus the ultrasonic energy primarily in a radial direction of the wheel instead of in the axial direction as required for the Veneer Grader. The wheels were modified for use in Metriguard's research into delamination of reconstituted wood products such as laminated veneer lumber (LVL). In that research, the modified transducer wheels are placed above and below the product, and a measure of the propagation time and/or attenuation of the stress wave is obtained. That research has been going on for several years with various signal processing methods employed. Similar methods have been employed by others (Shearer, et al. U.S. Pat. No. 4,750,368 and Shearer, et al. U.S. Pat. No. 4,856,334). In these patterns, methods are described wherein ultrasonic energy is introduced by a transducer on one side of a composite panel and received by another transducer on the other side of the panel. Received signal voltage based on amplitude or ringdown count, panel temperature and panel thickness are used to determine the quality of panel bonding. None of these methods have been used or have been suggested for use in the detection of wood finger joint quality or of lumber quality by passing stress waves transversely through the joints.

The present invention uses stress waves in the estimation of finger joint quality to avoid overstressing the joint, and new methods are disclosed for using the stress waves in the determination of wood finger joint quality and of lumber quality.

SUMMARY OF THE INVENTION

The present invention is method and apparatus for applying stress waves to wood with finger joints in a direction substantially perpendicular to the wood axis, measuring properties of the stress wave affected by the wood, extracting features to form a feature vector from the measured properties indicative of finger joint quality and using this feature vector to estimate finger joint quality.

In simplest form, one or more properties of a stress wave applied at a single point on the material in a neighborhood of the finger joint are measured. A neighborhood of the finger joint is any point near the finger joint including at the joint for which a stress wave, if caused to pass transversely through the wood at that point, would have its properties influenced by the quality of the finger joint. The stress wave properties include, for example, the propagation time required for the stress wave to pass transversely through the wood in a neighborhood of the finger joint, the amount of attenuation of the stress wave caused by its passage through the wood and the effects (amplitude and phase) on one or more frequency components of the stress wave caused by passage of the stress wave through the wood.

An example of an extracted feature is the stress wave velocity determined as the reciprocal of the ratio of the stress wave propagation time divided by the distance through the wood in the transverse direction over which the propagation time is measured. In this disclosure we define normalization as the process of adjusting the measurement to account for the propagation distance. In many cases this propagation distance is a relatively fixed dimension of the wood, for example thickness in lumber, and can be considered to be constant. In other cases this distance has enough variation that it also must be measured and used in normalizing the propagation time. Stress waves arranged so as to investigate stress wave propagation time through the width of the piece versus through the thickness will generally have a different normalization because of different cross-section width and thickness dimensions. Also, the thickness and/or width may vary along the length. Consequently, normalization may be required to give stress wave time per unit of distance. The dimensions may be entered as constants, or transducers for their measurement may be required. Similarly, it is known that stress wave propagation time is influenced by temperature (Pellerin, R. F. and Morschauser, C. R. 1973. Seventh Washington State University Symposium on Particleboard. Pullman, Washington), and depending on the temperature variation, it may or may not be necessary to measure temperature and include its effects in the measurement by known methods (Shearer, et al. U.S. Pat. No. 4,750,368 and Shearer, et al. U.S. Pat. No. 4,856,334).

One way to use the above feature for estimating finger joint quality is to test a sample consisting of a number of pieces of wood with finger joints. Testing would include measuring the stress wave time (and propagation distance and temperature if required), extracting the stress wave velocity feature and testing each finger joint to failure in the desired mode (tension for example). An estimator function can be developed by regression analysis which if applied to this data would establish the coefficients for a regression line giving the estimated quality of the finger joints (tensile strength) as a function of the stress wave velocity feature and in some cases temperature. In the case where only velocity is used, the feature vector is one-dimensional; if temperature is used also, the feature vector is two-dimensional. The estimated strength for a finger joint of unknown strength is the value of the regression equation evaluated at the feature vector (which here could be the stress wave velocity feature value alone or both it and temperature).

It is to be understood that estimator functions in this analysis refer generally to either linear or nonlinear functions of the selected feature vector. In the case where estimator functions are regressions, either linear or nonlinear regression may be implemented using well known principles.

If more than one feature is extracted, for example stress wave velocity and a measure of attenuation, then regression analysis could be used to establish, from the tested sample data, a regression equation giving estimated finger joint quality as a function of both stress wave velocity and attenuation feature values. As before, temperature may also be an independent variable (in this case it would be a third dimension of the feature vector). Then the estimated strength for a finger joint of unknown strength would be the value of the regression equation evaluated as a function of both the stress wave velocity feature value and also the stress wave attenuation feature (and possibly also temperature). (In this case, for illustrative purposes, the stress wave attenuation feature can be the unmodified stress wave measured property. It may be desirable to modify the attenuation measurement in the definition of this second feature as we did with the first feature where we started with stress wave propagation time measurement to obtain stress wave velocity.

More generally, one or more properties are measured of stress waves applied at a plurality of points about the surface of the material including points in a neighborhood of the finger joint. Then, features can be developed from the effect of the wood on stress wave properties at more than one location on the wood. This can be quite desirable because the effect of the wood away from the finger joint provides an effective reference for the effect of the wood near the finger joint. For example, stress waves can be applied at a sequence of measurement points distributed along the length of the wood. In that case a change in transverse propagation time from one value upward to a peak and then back down again as the measurements are taken at points along the length of the wood over a finger joint is indicative of a finger joint problem. The larger the rise in propagation time measured at the joint compared to its surroundings, the larger the finger joint problem. Large propagation times right at the finger joint as compared with those away from the joint could indicate lack of adhesive or other problem in the joint. Use of this property of the stress wave and others along with signal processing methods will become more clear with the following discussion of the preferred embodiment.

It has been observed experimentally that small stresses applied either in a tension, bending or torsional mode can enhance the ability of the present invention to detect marginal or poor quality finger joints. Each mode of stress application will tend to "open" different portions of the finger joint, and one or another or a combination of these stressing modes may be applicable for different situations. Evidently, the stress causes spaces to open in the interfaces between fingers of poorly bonded regions of the finger joint thereby creating significant changes in the stress wave properties measured.

OBJECTIVE AND ADVANTAGES

The objective of the present invention is to provide practical method and apparatus for nondestructively evaluating the quality of finger joints in finger-joined wood. An auxiliary objective is the categorization of the wood. Although the primary objective is to quantify the joint quality, the research performed has shown significant differences in stress wave property measurements made in the transverse direction through the wood. Thus, along with quantification of finger joint quality, a measure of wood quality is obtainable.

The advantages of this invention over the prior art are:
(a) The measurement is nondestructive compared to either bending or tensile proof loading which sometimes causes piece failure and handling problems in a part of the production process where it is awkward to deal with broken material.
(b) The size of the required apparatus is small compared with bending and tensile proof loading apparatus. Thus, the method can be implemented more efficiently than other methods in the production line.
(c) Measurements can be made rapidly enough to obtain detailed profile information along the piece and yet keep up with speeds of finger-joined lumber production.
(d) Information can be developed regarding inherent wood quality as well as finger joint quality. Thus the method can be used to grade short lengths of lumber destined for finger-joining.

The effectiveness, flexibility of operation and control, and simplicity of design and manufacture using the teachings of the present disclosure will become further apparent from the description of the preferred embodiment.

Research into this new concept has shown that stress wave property profiles obtained from measurements at a sequence of points on one or more longitudinal tracks along the wood length can be used effectively to identify the quality of finger joints. For example, an increase in stress wave propagation time is typically observed when the finger-joint passes between measurement transducers; further, the propagation time increase is greater for poor joints than for good joints.

BRIEF DESCRIPTION OF THE DRAWINGS

The preferred embodiment of the invention is illustrated in the accompanying drawings, in which:

FIG. 3 is a view of an ultrasonic transducer wheel.

FIG. 4 is another view of an ultrasonic transducer wheel.

FIG. 5 is an expanded view of the region where an ultrasonic transducer wheel transmitter and an ultrasonic transducer wheel receiver contact a piece of wood being tested.

The following disclosure of the invention is submitted in compliance with the constitutional purpose of the Patent Laws "to promote the progress of science and useful arts" (Article 1, Section 8).

DETAILED DESCRIPTION OF PREFERRED EMBODIMENT

Figure 1:
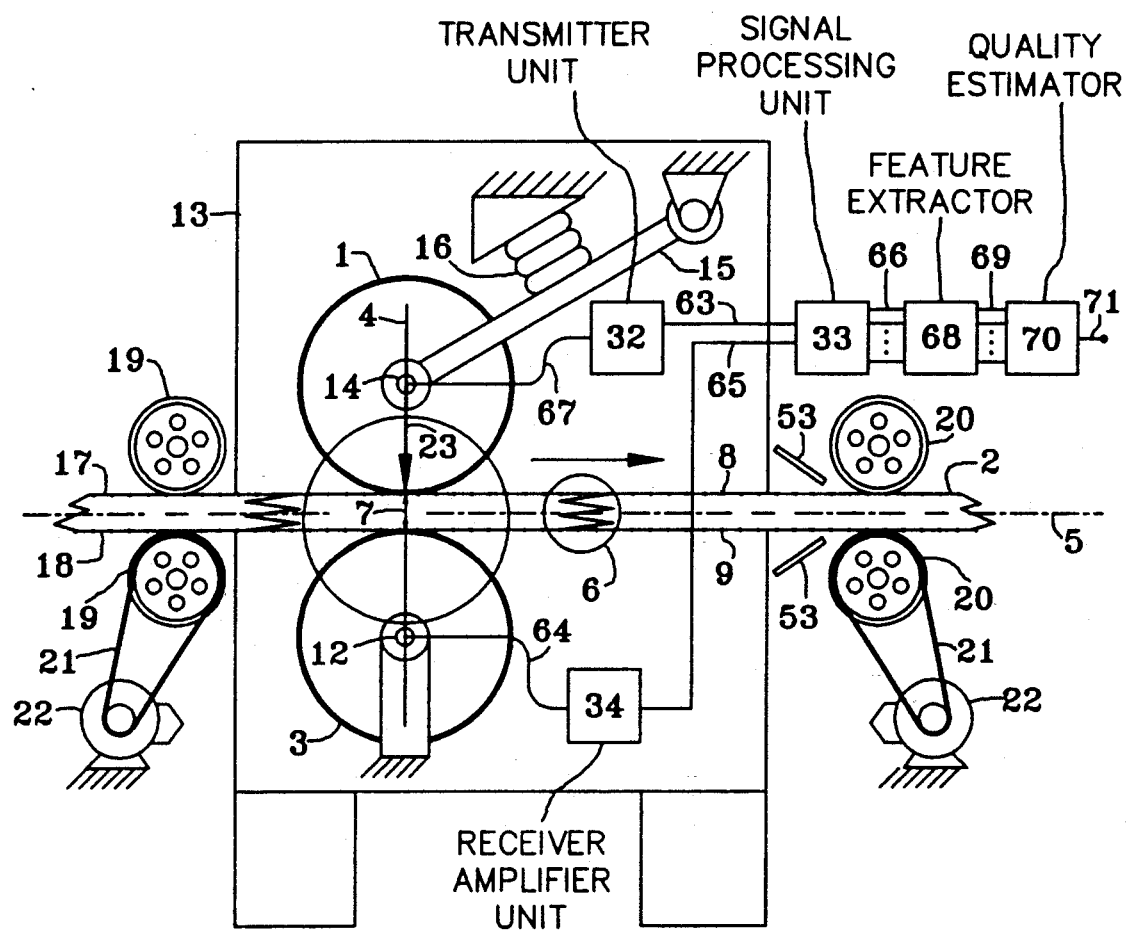
FIG. 1 is a schematic overview of the preferred embodiment.

FIG. 1 illustrates in overview the present invention. A means 1 for generating stress waves is located on one side of a piece of wood 2 to be measured, and a means 3 for receiving the stress waves is located on the opposite side of the piece of wood immediately opposite the generating means. It is understood that, while a straight line 4 connecting the generating means to the receiving means is substantially perpendicular to the longitudinal axis 5 of the wood, there may be reasons to offset either laterally or longitudinally the generator 1 (transmitter) or receiver 3 means somewhat from their exactly opposed positions. These reasons include mechanical arrangements for making the parts fit, or an arrangement may be desirable to force the stress wave through a greater extent of a finger joint area 6. In either case the normalizing distance may require adjustment to account for the distance 7 in the wood actually traveled by the stress wave from transmitter 1 to receiver 3.

Here, in the preferred embodiment, the means for generating stress waves is a rolling ultrasonic transducer wheel transmitter 1 which applies ultrasonic stress waves to one side of the wood 2 at a sequence of points 8 defining a track along the length of the wood. Another acceptable arrangement would cause relative motion of the wood transversely with respect to the transducers rather than the longitudinal relative motion described in this preferred embodiment. In that case, points would be scanned on a transverse track over the surface of the wood.

Figure 13:
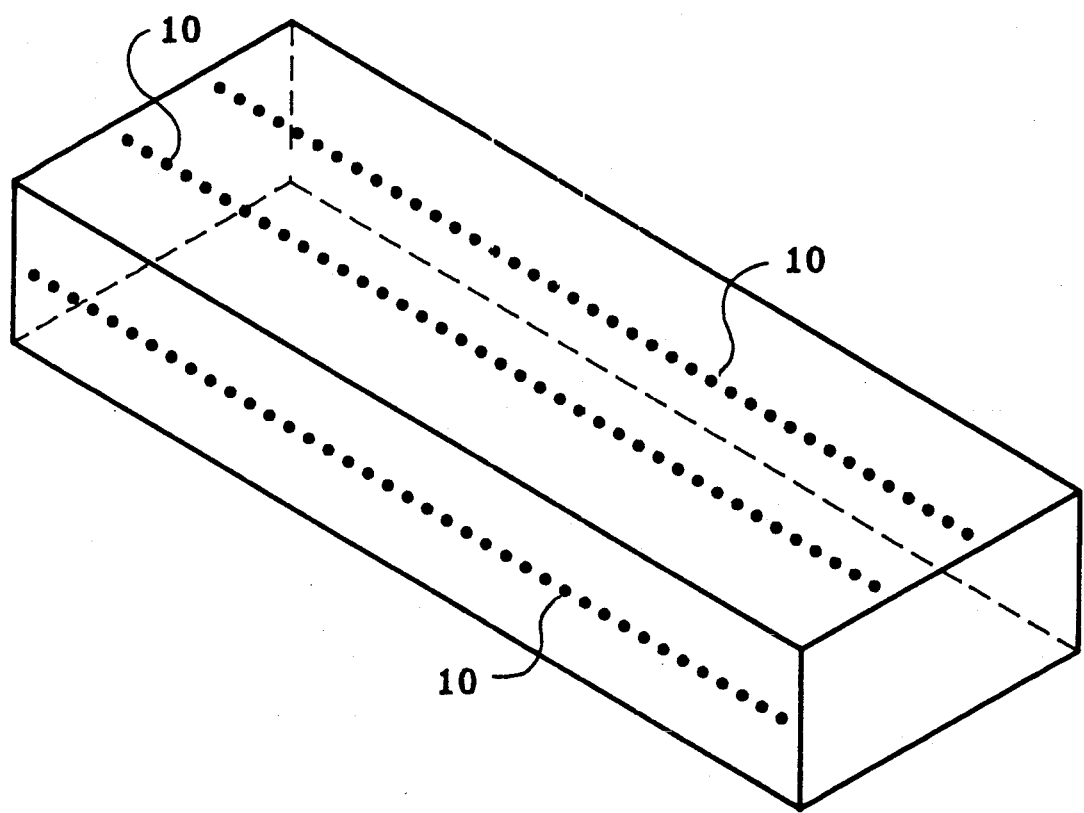
FIG. 13 is an isometric view of a piece of wood showing how three longitudinal tracks of measurement points could be located.

On the opposite side of the wood, the means for receiving the stress waves is an ultrasonic transducer wheel receiver 3 which senses the stress waves resulting from the transmitted stress waves. Voltages proportional to properties of the stress waves through the wood are developed at a sequence of measurement points 9 on the wood corresponding to the points 8 where the transmitter 1 applies the stress waves. The signal detected by the transducer wheel receiver 3 is treated and analyzed separately at each measurement point on the wood to give the transverse stress wave properties at that point. These properties can be treated individually or as functions of position along the wood length to give stress wave property profiles. Additional information can be obtained by performing the same type of measurement on a plurality of parallel longitudinal tracks spaced laterally about the surface of the lumber or a plurality of parallel lateral tracks spaced longitudinally along the lumber. In either case the stress wave properties can be treated pointwise as before or they can be developed as functions of longitudinal and lateral position. Normalization of the properties by propagation distance yields properties that are independent of the propagation distance. In this preferred embodiment, illustrative examples of stress wave times per unit of propagation distance are computed from stress wave measurements by dividing the measurements by distance (normalizing), and profiles developed from these normalized measurements are illustrated. FIG. 13 illustrates points along three longitudinal tracks 10, two of which are spaced on a wide face of a piece of lumber and one on a narrow face. These points represent locations where stress waves are applied. Corresponding points on opposite faces where signals are received are not shown in FIG. 13.

Figure 2:
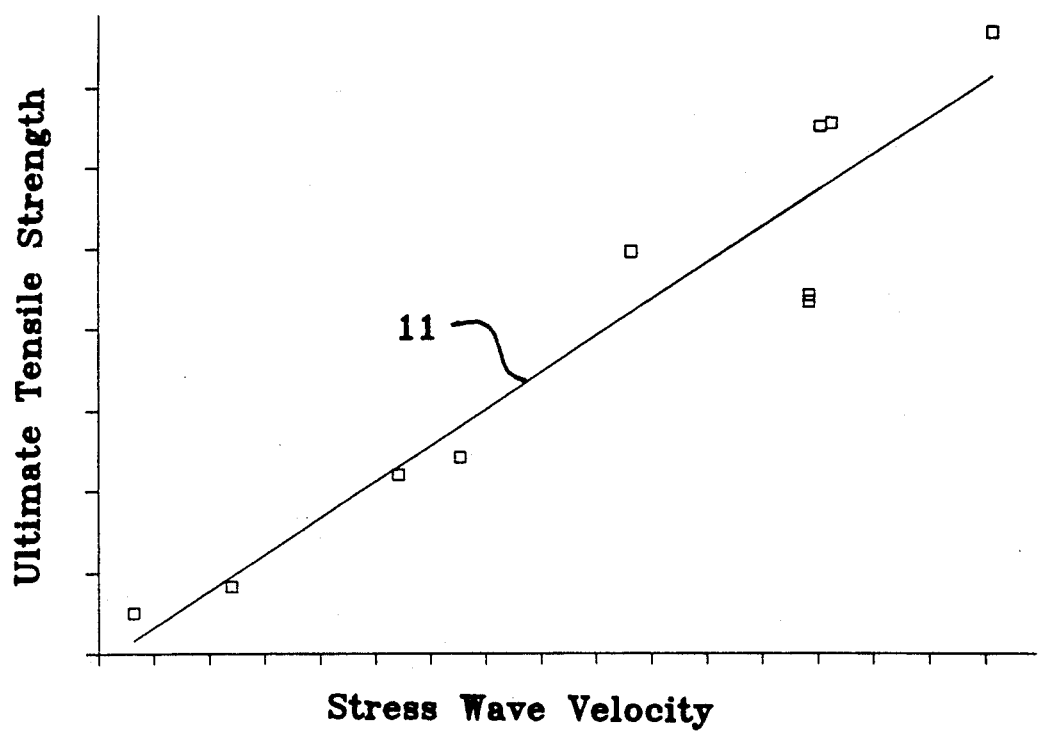
FIG. 2 is an example plot illustrating the relationship between ultimate tensile strength of finger joints and the feature, stress wave velocity. A linear regression line is shown along with experimental data.

If the data are analyzed at each point separately, decisions can be made about the quality of the wood or finger joint at each point. FIG. 2 is a plot of ultimate tensile strength (UTS) of finger joints in nominal 2×4 lumber (1.5 in×3.5 in [38 mm×89 mm]) versus the stress wave velocity feature, as computed from stress wave times measured transversely through the 1.5 in [38 mm] dimension of the wood at finger joints. In this case, each computation of stress wave velocity is determined from an average of three stress wave time measurements at three different lateral locations longitudinally positioned at a finger joint. FIG. 2 is representative of the type of results expected from transverse stress wave measurements. FIG. 2 shows clearly a trend of greater finger joint strengths for greater stress wave velocities, and the linear regression line 11 of UTS on stress wave velocity also shown in FIG. 2 is a useful estimator for UTS as a function of stress wave velocity.

When the transducer wheels are on opposite sides of a finger joint, the stress wave is propagated through a volume of wood containing several fingers. If the adhesive bond is good, little additional attenuation or delay over that of solid wood is observed through this region. However, if the bond is poor due to any of a number of causes in one or more regions through which the stress wave must pass, the stress wave will be attenuated and/or delayed.

At poor quality finger joints, the measured value of stress wave propagation time is greatest; thus poor joints are detectable by dealing with the measurements individually and thresholding the signal into quality categories. This does not require prior knowledge of joint location; large propagation times are categorized as poor joints. There are situations where poor wood properties will cause a section of wood to be categorized as a poor quality finger joint when actually there is no finger joint present. This is not viewed as being detrimental because wood quality is just as important as finger joint quality. Indeed, the same method and apparatus can be used to estimate the quality of lumber without finger joints at measurement points along its length by stress wave property measurements.

However, the preferred embodiment includes another signal processing method which enhances the ability of the system to quantify finger joint quality. This method determines change in signal wherein an effective differentiation is achieved by forming the difference between values of the signal and preceding values along the length of the piece. Measurements at more than one point are used for each decision of finger joint quality level. In the case where measurements are made at more than one point about each cross section for a specific longitudinal position, a measure of similarity of difference among the measurements can be useful to indicate consistency over the cross section. In FIG. 2 an average of three measurements was used at each longitudinal position considered. The reliability in determining the seriousness of finger joint defects by using more than one measurement at each longitudinal position is generally improved over the situation where only one measurement is used. The dispersion or estimated standard deviation of the measurements at each longitudinal position could have been computed and used also as a feature for determining quality of the finger joint. There are many other quantities comparing the stress wave property values from a plurality of laterally spaced measurements at each longitudinal location that can be computed.

In FIG. 1 ultrasonic transducer transmitter wheel 1 is shown contacting a piece of finger-joined lumber 2 under test. Ultrasonic transducer receiver wheel 3 is shown contacting the lumber from the side opposite the transmitter wheel. All of the concepts discussed apply equally well with the positions of the transducer wheels reversed or with the wheels contacting the lumber on the edges rather than over and under as shown. In FIG. 1, the axle 12 of wheel 3 is shown fixed to a frame 13 whereas the axle 14 of wheel 1 is slung on a beam 15 with pressure applied by inflatable air spring 16 so as to squeeze the lumber 2 between the two transducer wheels to effect a good coupling path for the ultrasonic stress wave energy into and from the lumber. The transducer wheels 1 and 3 are shown immediately opposite one another on opposite surfaces 17 and 18 of the lumber 2. In some cases it may be advantageous to offset the wheels from one another either in the lateral direction from the lumber axis or in the longitudinal direction. In that case the propagation path length through the lumber is increased, and any distance normalization factors used must be adjusted accordingly. The lumber is carried through the tester by drive roller pairs 19 and 20 placed before and after the transducer wheels 1 and 3. Rollers 19 and 20 are mounted on bearings and driven by belts 21 and motors 22 to provide motive force to the lumber without introducing noise that would cause false signals at receiver transducer wheel 3. The drive rollers 19 and 20 squeeze the lumber and are ganged together in pairs at the infeed and outfeed so that the infeed rollers 19 turn at the same speed but in opposite directions and the outfeed rollers 20 also turn at the same speed but in opposite directions to drive the lumber.

Transmitter and receiver transducer wheels respectively are fabricated as shown in FIGS. 3, 4 and 5. These transducers are a modification of the transducer wheels disclosed in U.S. Pat. No. 4,201,093. A major difference is that the ultrasonic energy is directed radially as shown by arrow 23 instead of primarily in the axial direction as described in U.S. Pat. No. 4,201,093. This is accomplished by mounting piezoelectric elements 24 so that their axes are aligned with radii of the transducer wheels. The feet 25 of the piezoelectric elements are molded of structural epoxy, e.g. Hysol No. EA934 NA Parts A and B available from Dexter Adhesives & Structural Materials Division, Pittsburgh CA, so that their surfaces 26 are cylindrical in shape to match the interior cylindrical surfaces of the aluminum shells 28 of the transducer wheels 1 and 3. Another difference from U.S. Pat. No. 4,201,093 is the annular rib 62 formed into the outer circumference of each transducer wheel as shown most clearly in FIG. 4. Its purpose is to better define the contacting region of the transducer wheel to the tested wood and hence the track location. The annular rib shown has a circular section which contacts the wood, but this is not essential; other shapes can be used depending on the contact pressure and the amount of contact area deemed desirable for the type of wood tested. The conical focusing ring described in U.S. Pat. No. 4,201,093 is not used. In the case of the transmitter transducer wheel 1, a transformer 29 is used to increase the driving voltage available to drive the piezoelectric element and hence the strength of the signal out of the transducer wheel. Details of the fluid couplant filling the cavity of the transducer wheels and acting to couple the ultrasonic energy from the piezoelectric element into the cylindrical aluminum shell in the case of the transmitter or from the shell in the piezoelectric element in the case of the receiver are discussed in U.S. Pat. No. 4,201,093 as are other details of these transducer wheels. Other transducer wheels such as the ones described in U.S. Pat. Nos. 4,750,368 and 4,856,334 may also be used.

Referring to FIGS. 1 and 5, a voltage pulse is developed in electronic transmitter unit 32 to drive the piezoelectric element 24 in transmitter wheel 1, and a reference 63 from this pulse is sent to signal processing unit 33. Receiver amplifier unit 34 conditions the signal 64 received from receiver wheel 3, and the conditioned signal 65 is sent to signal processing unit 33. The signal processing unit 33 compares the conditioned received signal 65 with the transmitter reference 63 and determines the measured stress wave properties 66, for example stress wave propagation time, attenuation, effects on one or more frequency components and other stress wave properties being used. It is understood that while distance and temperature measuring transducers are not shown in FIG. 1, these could be used to provide the signal processing unit 33 with measures of propagation distance and temperature if they are required for normalization of the stress wave properties. Methods for achieving these results are well known to a person skilled in the art. Details of signal processing to develop the stress wave propagation time property which is a measure of the time from incidence of the transmitter ultrasonic drive signal 67 applied at the transmitter transducer wheel to reception of a signal 64 at the receiver transducer wheel are disclosed in U.S. Pat. No. 4,201,093. Because of the generally shorter propagation distances involved here than those for U.S. Pat. No. 4,201,093, the noise removal methods described there usually are not needed for the present invention, although in some unusually noisy situations they may be useful.

Figure 6:
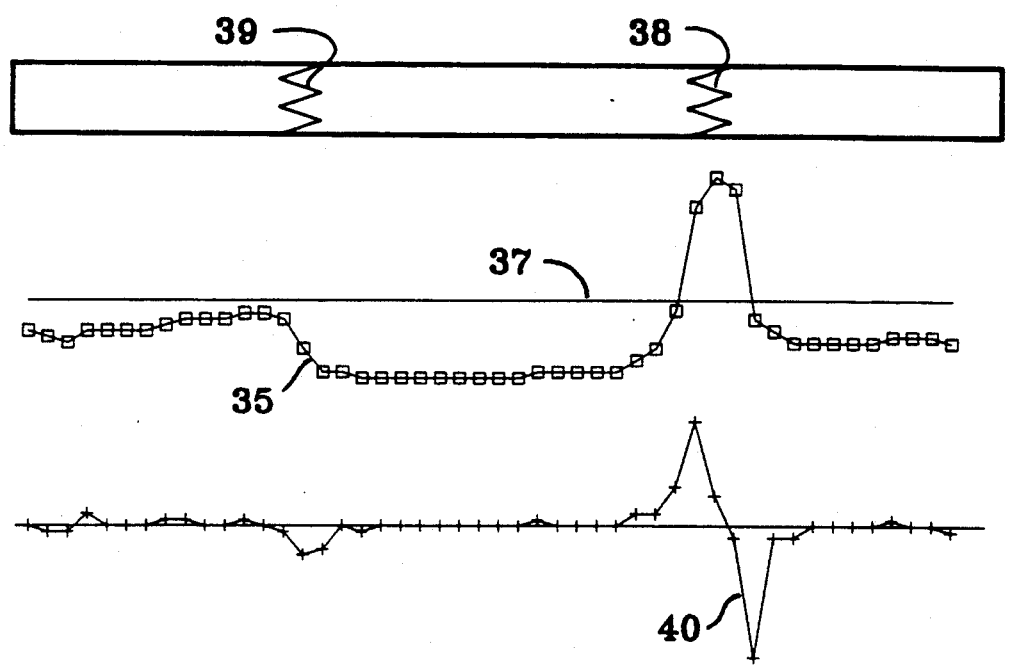
FIG. 6 illustrates a piece of lumber with one good and one poor finger joint. Corresponding to a sequence of measurements along the lumber, plots of normalized stress wave times and a difference function developed from these times are shown.

FIG. 6 illustrates a normalized stress wave propagation time profile signal 35 as a function of distance along a finger joined piece of lumber 36. This signal can be compared against threshold 37 for characterization into good and bad regions according to their stress wave propagation times. Poor finger joint 38 shows up as having a large propagation time which exceeds threshold 37 and good finger joint 39 has propagation time not exceeding the threshold. Note that the wood itself can exhibit differences from one side of the finger joint to the other, and if the threshold 37 is set too low, the stress wave time for the wood may exceed the threshold set for poor finger joints. This information is itself useful as a wood quality detector.

Signal processing can help sort finger joints from wood as well as help quantify finger joint quality. For example, a differencing operation wherein each measured stress wave time value is added to the negative of the measured stress wave time value at the preceding location along the wood gives a signal that is zero for locations where the stress wave values are constant. But, where change occurs, this difference function is large. The differencing operation tends to make regions stand out where changes in stress wave propagation time occur and suppress regions where the stress wave propagation time is constant. In those cases where finger joints join two pieces of wood that are dissimilar in stress wave propagation time, the difference function can be expected to show the joined region. If the finger joint itself shows a difference in stress wave propagation time, this feature will also show up in the difference function. FIG. 6 illustrates also the difference function 40 obtained from function 35.

Figure 7:
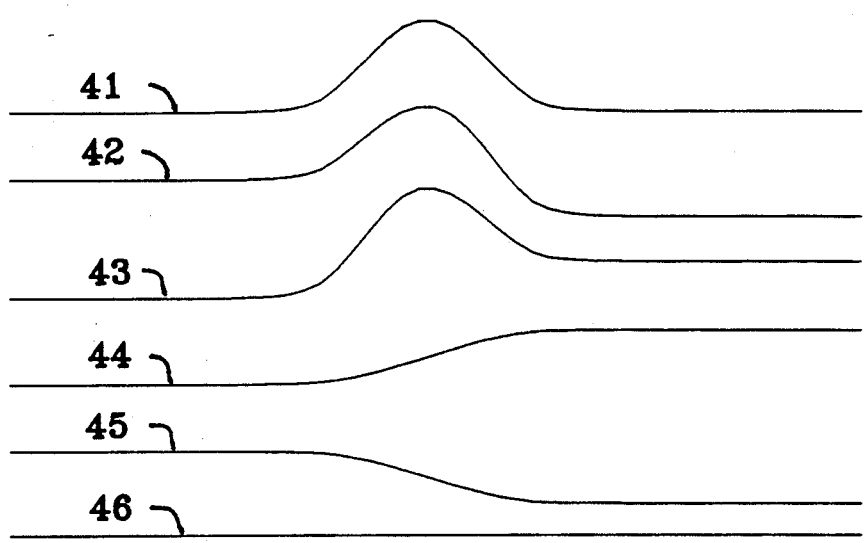
FIG. 7 is illustrative of the types of stress wave time waveforms that will be observed as a function of position along the length of a piece of wood including a finger joint.

FIG. 7 illustrates the types of stress wave time signal profiles that generally will be observed in the neighborhood of a finger joint. Signal 41 represents a typical joint showing approximately equal stress wave times on both sides of the joint and a slightly greater stress wave time at the joint. Signals 42 and 43 represent situations where stress wave times on one side of the joint are different from the other but the time at the joint is greater than for either wood segment. Signals 44, 45 and 46 represent smooth transitions of stress wave times from one wood segment through the joint to the other wood segment without an increase in time at the joint. These finger joints would be classified as good joints. Signal profile 46 represents the situation where the wood stress wave time measurements are the same on both sides of the finger joint with no increase seen at the joint. The good finger joint of signal 46 is not detectable from processing of this stress wave time signal profile.

Figure 8:
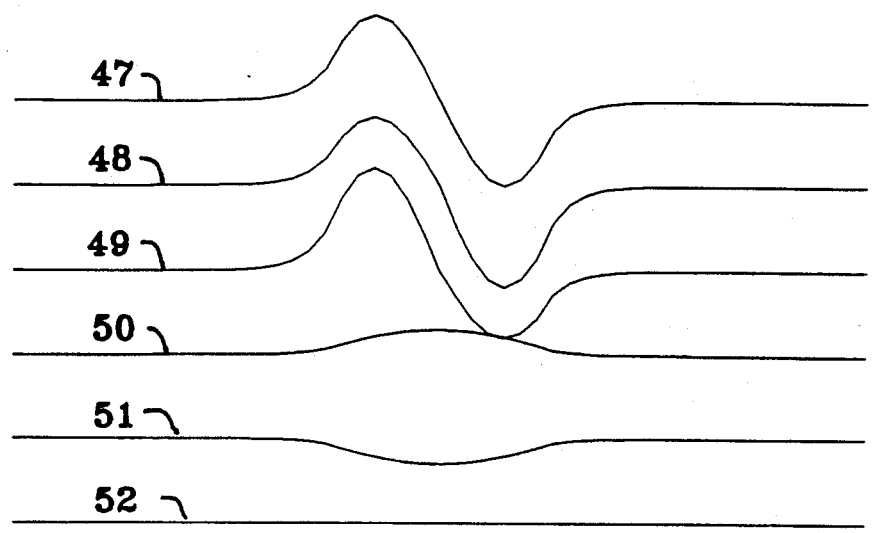
FIG. 8 shows the result of applying a differencing operation to the functions of FIG. 7.

Curves 47 through 52 of FIG. 8 illustrate respectively the result of applying the above described differencing operation to the signals 41 through 46 of FIG. 7. Although there are many different features that can be developed to describe finger joint quality from stress wave properties, one feature that successfully quantifies finger joint quality in lumber is described here. This feature is extracted from difference waveform according to the following described algorithm.

As the finger-joined piece of lumber passes between the transducer rollers 1 and 3, the difference function $D(x)$ is computed from the normalized stress wave time measurement $S(x)$ at each of a sequence of positions $x = \{x_i\}$, $i = 1, 2, \ldots$ along the lumber length according to $D(x_i) = S(x_i) - S(x_{i-1})$. The algorithm looks first for a negative-going zero crossing of the signal $D(x)$; suppose it occurs at position $x = x_j$. Then, the maximum $D_1$ of the signal $D(x)$ is determined over a domain $(x_j - H < x < x_j)$. immediately before the zero crossing, and the minimum $D_2$ is determined over a domain $(x_j < x < x_j + H)$ immediately after the zero crossing. The distance H is the maximum length over which a finger joint might have an effect on the stress wave time measurement. The extracted feature is: $Q = \min[D_1, -D_2]$. Smaller Q is higher quality and larger Q is lower quality. It is clear that classifying grade thresholds applied directly to Q will cause the finger joint to be assigned to one of several grades depending on the value of Q and which category it is placed in according to the thresholds. In this case implementation would not require the development of an estimating function, rather feature value Q by itself is sufficient to identify quality. However, as an example, one could define the reciprocal $1/Q$ as the estimator function because $1/Q$ increases with quality, and that may be desirable in some situations. Details of methods for implementing this algorithm according to the description given are well known to a person skilled in the art.

Figure 9:
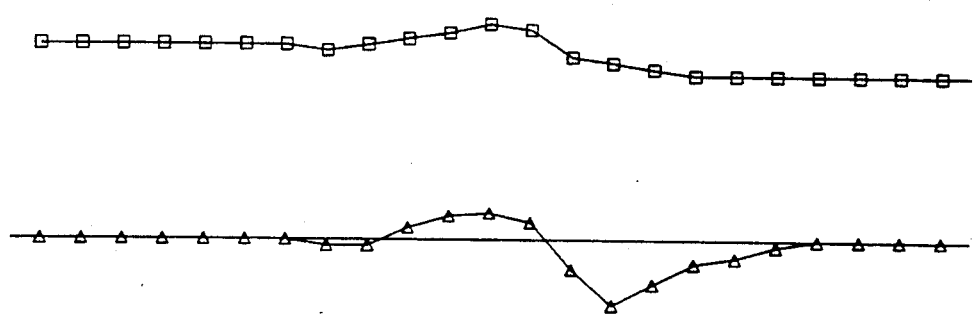
FIG. 9 is a plot of actual stress wave time per unit distance data versus position along the length of nominal 2×4 lumber including a good quality finger joint. Also illustrated is a difference function from a differencing operation.
Figure 10:
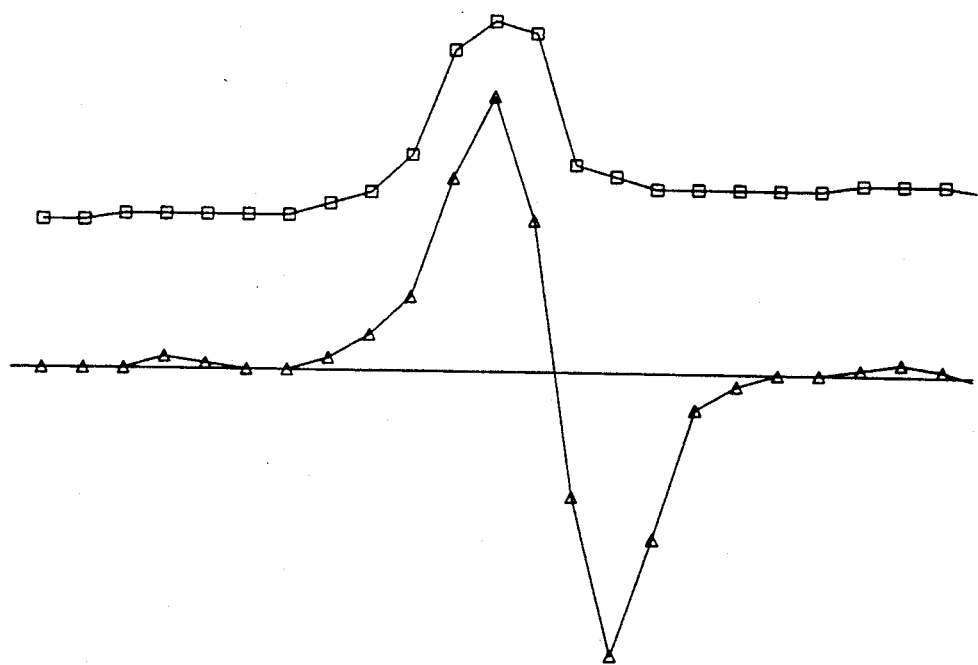
FIG. 10 is another example of actual data similar to FIG. 9 but with a poor quality finger joint.

FIGS. 9 and 10 illustrate actual normalized stress wave time functions $S(x)$ and the difference functions $D(x)$ for two different finger joints in nominal $2 \times 4$ lumber. The functions $S(x)$ are measured at 5 mm increments along each piece over a section including the finger joint in question. Here the difference function is defined differently than before according to: $D(x_i) = S(x_i) + S(x_{i-1}) - S(x_{i-2}) - S(x_{i-3})$. The purpose of adding two measurements and subtracting two measurements is to reduce the noise level seen if just the adjacent different is computed. This definition of the difference function causes a fixed shift (delay) in the position where the finger joint is sensed. In this case the shift is 1.5 measurement intervals or 7.5 mm. Also, an initialization step is required wherein, usually, we would set $D(x_1) = D(x_2) = D(x_3) = 0$. In the previously mentioned differencing operation where $D(x_i) = S(x_i) - S(x_{i-1})$, the shift is 0.5 measurement intervals or 2.5 mm and the initialization is $D(x_1) = 0$. From data used to plot FIGS. 9 and 10 respectively, the values Q are 1.2 and 12.2. From these Q data, the finger joint in FIG. 10 is estimated to be much inferior in quality to the finger joint in FIG. 9. We define the class of differencing operations to include any operation such as the type mentioned above which tend to enhance differences in quality of one finger joint from another. More generally, we include in this definition of the class of differencing operations any matched filtering operation. The use of matched filters is well known to a person skilled in the art, and the specific differencing operations disclosed can be shown to be special cases of matched filtering operations.

In FIG. 1, a bending stress to the wood at the measurement point can be achieved by displacing the mounting of both the transmitter and receiver ultrasonic transducer wheels 1 and 3 upward or downward relative to the drive rollers 19 and 20. Guides 53 cause lead ends of the lumber pieces to be directed between the outfeed drive rollers 20 so that a bending span between the drive roller sets is accomplished. A tensile stress can be achieved by applying a differential torque to the outfeed drive rollers 20 as compared to the infeed drive rollers 19 so that a tensile force is applied to the wood between the infeed and outfeed rollers. One means for doing this is to apply different frequency drive signals to induction motors providing motive force at the infeed and outfeed drive rollers. This causes the motors to operate with different slip frequencies and hence at different torques. Frequency converters for this purpose are readily available. A torsional stress can be applied to the wood in the region of test by canting the axes of the infeed drive rollers 19 and outfeed drive rollers 20 with respect to each other. It is clear that by these means any combination of bending, tensile and torsional stress can be applied within practical engineering limitations.

Although the extraction of one feature from stress wave time profiles and its application in the estimation of finger joint quality as just described has been proved successful, it is to be understood that a plurality of features can be extracted to form a feature vector and applied in the estimation of finger joint quality or of wood quality. Further, it is to be understood that one or more features from more than one track of data about the lumber cross section can be extracted for use in estimating finger joint quality or wood quality. FIG. 1 shows stress wave properties 66 entering feature extractor 68, and features 69 entering quality estimator 70. The quality 71 can be used with known methods to control sorting, marking cutting and other operations.

One method for extracting a feature from more than one track of data is to average the normalized stress wave times, the average being taken at each lumber cross section over all the track values measured at that cross section. Then, the above methods for obtaining a difference function and for obtaining Q can be applied to the average function.

Figure 11:
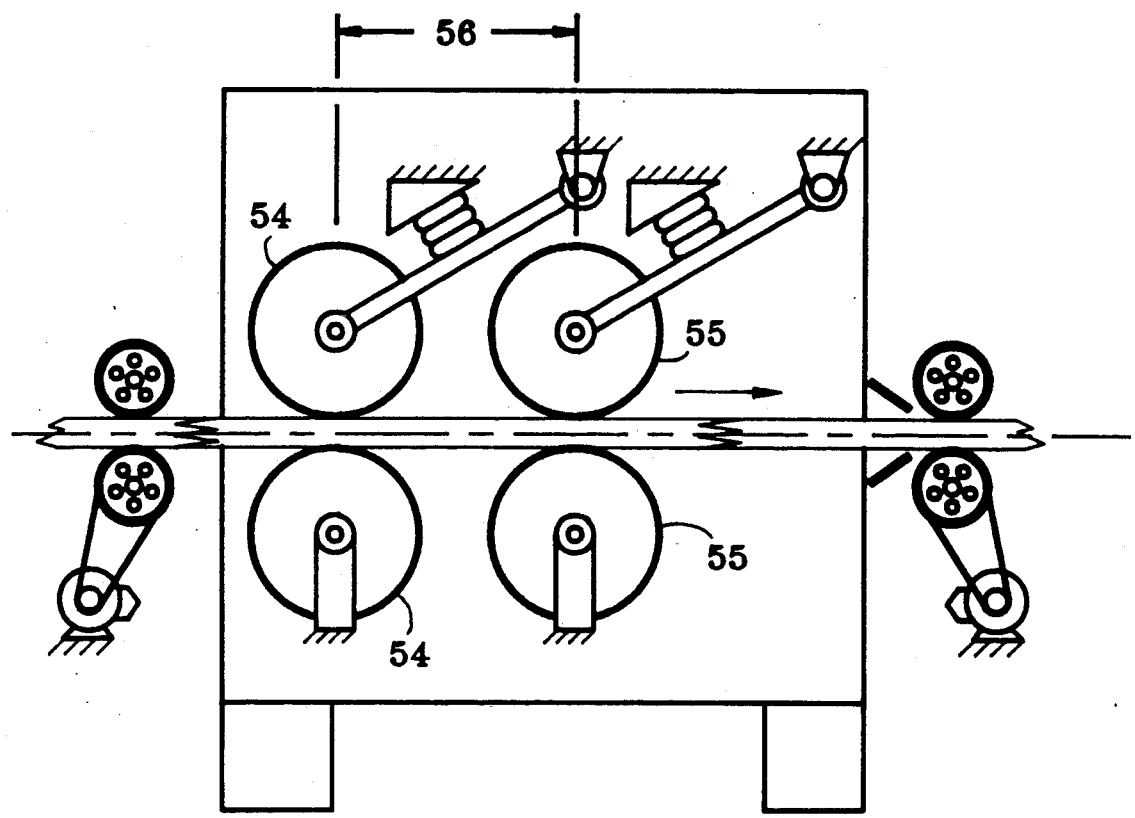
FIG. 11 is an elevation view illustrating how two sets of rolling transducer wheels could be positioned for obtaining data from two tracks along a piece of wood.
Figure 12:
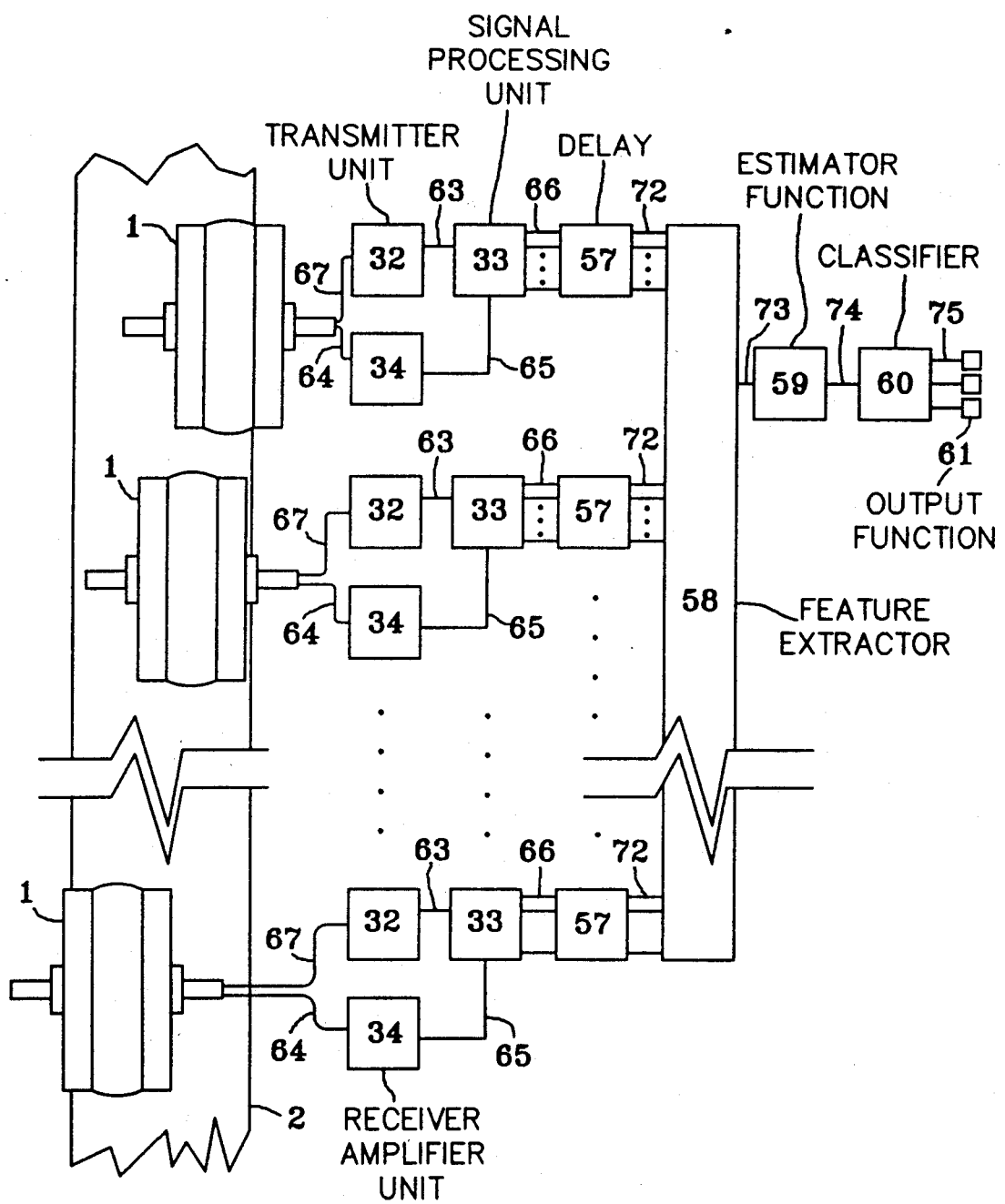
FIG. 12 is a plan view of multiple sets of rolling transducer wheels of and illustrates how they are displaced laterally for measurements along multiple longitudinal tracks. It also includes a general schematic diagram illustrating how processing can occur when more than one track of data is being taken.

In the case where stress wave time measurements are made along multiple tracks, some longitudinal displacement of the measurement transducer wheels may be required for the different tracks as shown by the elevation view in FIG. 11 for two tracks where track 1 transducers 54 are placed upstream from track 2 transducers 55. Fixed longitudinal displacement 56 of the track 2 transducers from the track 1 transducers cause fixed distance delays for the data along the piece, and that can be compensated by appropriately storing the data in memory with corresponding time delays. FIG. 12 illustrates a schematic plan view of multiple transducers sets and shows a lateral displacement of transducer wheels for multiple data tracks. The data processing shown in FIG. 12 shows electronic transmitter units 32 which drives transmitter wheels 1, receiver amplifier units 34 which condition signals from receiver wheels (hidden in this view below the wood and transmitter wheels), signal processing units 33 which develop the stress wave properties 66 as previously described, delays 57 which bring into longitudinal synchronism the properties from the several tracks to give delayed properties 72, a feature extractor 58 which extracts one or more features indicative of the wood or finger joint quality, and an estimator function 59 which determines quality 74 as a function of the vector 73 of features, a classifier 60 which thresholds quality into categories 75, and output functions 61. The delayed properties 72 from all the transducer sets are used in the feature extractor and estimator function to determine quality 74. If desired, a classifier 60 categorizes the finger joints and/or the wood into one of several grade categories 75. Output of the classifier can direct output functions 61 which could be a sorting process where the wood is put into grades for sale, a trimming process where identified poor finger joints or other poor areas are removed by trimming, and/or a marking process where quality identification marks are placed on the wood.

FIG. 13 illustrates an isometric view showing points of application of stress waves along three longitudinal tracks about the cross section of a piece of lumber. Note that one of the tracks is along the edge of the lumber and for that case the transducer wheels would have their axles oriented at right angles to the transducers for the other tracks.

In compliance with the statute, the invention has been described in language more or less specific as to structural features. It is to be understood, however, that the invention is not limited to the specific features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A method for estimating the quality of a finger joint in a piece of wood comprising the following steps:
   causing a stress wave to pass through the piece of wood in a neighborhood of the finger joint, the direction of propagation of the stress wave being substantially perpendicular to the longitudinal axis of the piece of wood;
   measuring one or more properties of the stress wave affected by passage of the stress wave through the wood; and
   using information derived from the measured property or properties to estimate the finger joint quality.

2. The method of claim 1 wherein one of the measured stress wave properties is the propagation time required for the stress wave to pass through the wood.

3. The method of claim 1 wherein one of the measured stress wave properties is the amount of attenuation of the stress wave caused by passage of the stress wave through the wood.

4. The method of claim 1 wherein one of the measured stress wave properties is the effect the finger joint has on a frequency component of the stress wave caused by passage of the stress wave through the wood, the effect being a change in either amplitude or phase of the frequency component.

5. The method of claim 1 wherein the step of using information derived from the measured property or properties to estimate finger joint quality involves using an estimator function with coefficients determined by test data, the estimator function being a function whose domain is a feature vector extracted from one or more stress wave property values and whose range is the estimated finger joint quality.

6. The method of claim 1 including additionally the step of applying either a bending, tensile or torsional stress to the wood while measuring properties of the stress wave.

7. A method for estimating the quality of a finger joint in a piece of wood comprising the following steps:
   causing stress waves to pass through the wood in directions substantially perpendicular to the longitudinal axis of the wood and at a plurality of locations about the wood surface including a neighborhood of the finger joint;
   measuring at each of the plurality of locations one or more properties of the stress waves affected by passage of the stress waves through the wood;
   extracting from the measurements one or more features indicative of finger joint quality; and
   using the extracted feature or features to estimate the finger joint quality.

8. The method of claim 7 wherein one of the measured stress wave properties is the propagation time required for the stress waves to pass through the wood.

9. The method of claim 7 wherein one of the measured stress wave properties is the amount of attenuation of the stress waves caused by passage of the stress waves through the wood.

10. The method of claim 7 wherein one of the measured stress wave properties is the effect the wood has on a frequency component of the stress waves caused by passage of the stress waves through the wood, the effect being a change in either amplitude or phase of the frequency component.

11. The method of claim 7 including additionally the step of applying either a bending, tensile or torsional stress to the wood while measuring properties of the stress wave.

12. The method of claim 7 wherein the step of extracting one or more features includes forming a difference function, the difference function being the result of a differencing operation applied to stress wave property values of a property measured at each of the plurality of locations.

13. The method of claim 12 wherein the step of extracting one or more features comprises the substeps of:
   finding a negative going zero crossing of the difference function;
   obtaining a maximum value $D_1$ of the difference function in a domain immediately preceding the zero crossing;
   obtaining a minimum value $D_2$ of the difference function in a domain immediately succeeding the zero crossing; and
   defining a feature Q given by:

$$Q = \text{Min}[D_1, -D_2]$$

where large Q is indicative of poor quality finger joints, and small Q is indicative of good quality finger joints.

14. The method of claim 7 wherein the step of using the extracted feature or features to estimate the finger joint quality involves using an estimator function with coefficients determined by test data, the estimator function being a function whose domain is a feature vector extracted from one or more stress wave property values and whose range is the estimated finger joint quality.

15. Apparatus for estimating the quality of a finger joint in a piece of wood comprising:
   means for passing stress waves through the wood in a neighborhood of the finger joint and in a direction substantially perpendicular to the longitudinal axis of the wood;
   means for measuring one or more properties of the stress wave after it has passed through the wood; and
   means for using the information derived from the measured property or properties to estimate the finger joint quality.

16. The apparatus of claim 15 wherein the means for measuring one or more properties of the stress wave includes means for measuring the propagation time required for the stress wave to pass through the wood.

17. The apparatus of claim 15 wherein the means for measuring one or more properties of the stress wave includes means for measuring the stress wave attenuation caused by passage of the stress wave through the wood.

18. The apparatus of claim 15 wherein the means for measuring one or more properties of the stress wave includes means for measuring the effect on a frequency component of the stress wave caused by passage of the stress wave through the wood, the effect being a change in either amplitude or phase of the frequency component.

19. The apparatus of claim 15 including additionally a means for applying either a bending, tensile or torsional stress to the wood while measuring properties of the stress wave.

20. The apparatus of claim 15 wherein the means for using information derived from the measured property or properties to estimate finger joint quality includes means for using an estimator function with coefficients determined by test data, the estimator function being a function whose domain is the space of one or more measured property values and whose range is the estimated finger joint quality.

21. Apparatus for estimating the quality of a finger joint in a piece of wood comprising:
   means for causing stress waves to pass through the wood in directions substantially perpendicular to the longitudinal axis of the wood and at a plurality of locations about the wood surface including a neighborhood of the finger joint;
   means for measuring one or more properties of the stress waves at each of the plurality of locations;
   means for extracting one or more features indicative of finger joint quality from the measurements; and
   means for using the extracted feature or features to estimate the finger joint quality.

22. The apparatus of claim 21 wherein the means for measuring one or more properties of the stress waves includes means for measuring the propagation time required for the stress waves to pass through the wood.

23. The apparatus of claim 21 wherein the means for measuring one or more properties of the stress waves includes means for measuring stress wave attenuation caused by passage of the stress waves through the wood.

24. The apparatus of claim 21 wherein the means for measuring one or more properties of the stress waves includes means for measuring the effect on a frequency component of the stress waves caused by their passage through the wood, the effect being a change in either amplitude or phase of the frequency component.

25. The apparatus of claim 21 including additionally a means for applying either a bending, tensile or torsional stress to the wood while measuring properties of the stress wave.

26. The apparatus of claim 21 wherein the means for extracting one or more features indicative of finger joint quality includes a means for forming a difference function, the difference function being the result of a differencing operation applied to stress wave property values of a property measured at each of the plurality of locations.

27. The apparatus of claim 22 wherein the means for extracting one or more features indicative of finger joint quality also includes:
   means for finding a negative going zero crossing of the difference function;
   means for obtaining a maximum value $D_1$ of the difference function in a domain immediately preceding the zero crossing;
   means for obtaining a minimum value $D_2$ of the difference function in a domain immediately succeeding the zero crossing; and
   means for computing a feature Q given by $Q = \text{Min}[D_1, -D_2]$, where large Q is indicative of poor quality finger joints, and small Q is indicative of good quality finger joints.

28. The apparatus of claim 21 wherein the means for using the extracted feature or features to estimate the finger joint quality includes means of using an estimator function with coefficients determined by test data, the estimator function being a function whose domain is a feature vector extracted from one or more stress wave property values and whose range is the estimated finger joint quality.

* * * * *